(12) United States Patent
Farris

(10) Patent No.: US 9,603,630 B2
(45) Date of Patent: Mar. 28, 2017

(54) ROTATABLE BASE MULTI-AXIAL SCREW ASSEMBLY

(75) Inventor: Robert A Farris, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 604 days.

(21) Appl. No.: 13/097,977

(22) Filed: Apr. 29, 2011

(65) Prior Publication Data

US 2012/0277805 A1 Nov. 1, 2012

(51) Int. Cl.
*A61B 17/70* (2006.01)

(52) U.S. Cl.
CPC ................................. *A61B 17/7037* (2013.01)

(58) Field of Classification Search
CPC . A61B 17/70; A61B 17/7001; A61B 17/7032; A61B 17/7034; A61B 17/7035; A61B 17/7037; A61B 17/7038; A61B 17/7041; A61B 17/7043; A61B 17/7046; A61B 17/8605
USPC .................. 606/246–279, 300–320
See application file for complete search history.

(56) References Cited

U.S. PATENT DOCUMENTS

| | | | |
|---|---|---|---|
| 7,524,323 B2* | 4/2009 | Malandain | 606/246 |
| 8,002,806 B2* | 8/2011 | Justis | 606/264 |
| 8,083,776 B2* | 12/2011 | Alvarez | 606/265 |
| 8,100,946 B2* | 1/2012 | Strausbaugh et al. | 606/266 |
| 8,221,472 B2* | 7/2012 | Peterson et al. | 606/270 |
| 8,277,490 B2* | 10/2012 | Freeman et al. | 606/266 |
| 8,337,530 B2* | 12/2012 | Hestad et al. | 606/279 |
| 8,628,558 B2* | 1/2014 | Harvey et al. | 606/267 |
| 2004/0097933 A1* | 5/2004 | Lourdel et al. | 606/61 |
| 2005/0080420 A1* | 4/2005 | Farris et al. | 606/61 |
| 2005/0203515 A1* | 9/2005 | Doherty et al. | 606/61 |
| 2007/0090238 A1* | 4/2007 | Justis | 248/181.1 |
| 2010/0145394 A1* | 6/2010 | Harvey et al. | 606/302 |
| 2010/0204735 A1* | 8/2010 | Gephart et al. | 606/264 |
| 2010/0305620 A1* | 12/2010 | Gotfried | 606/305 |
| 2011/0112578 A1* | 5/2011 | Keiser et al. | 606/264 |
| 2012/0016425 A1* | 1/2012 | Shaffrey et al. | 606/305 |
| 2012/0078307 A1* | 3/2012 | Nihalani | 606/264 |
| 2012/0130436 A1* | 5/2012 | Haskins et al. | 606/305 |
| 2012/0185003 A1* | 7/2012 | Biedermann et al. | 606/328 |
| 2012/0277806 A1* | 11/2012 | Smith et al. | 606/308 |

FOREIGN PATENT DOCUMENTS

WO WO 2010103198 A1 * 9/2010

* cited by examiner

*Primary Examiner* — Pedro Philogene
*Assistant Examiner* — Lynnsy Summitt

(57) ABSTRACT

A multi-axial screw assembly comprises a receiver member, a base member, a crown and a bone anchoring member. The receiver member has an aperture configured to receive the base member and an internal groove. The base has a deflectable ring configured to mate with the internal groove of the receiver member and a slot configured to allow the deflectable ring to compress to a diameter less than the diameter of the aperture such that the base member may be compressed and axially received within the receiver member. The base member is axially restrained within the base member relative to the receiver member while allowed to rotate relative to the receiver member. The crown is received within the receiver member along the central axis of the receiver member. The crown maintains the diameter of the deflectable ring greater than the diameter of the aperture.

20 Claims, 2 Drawing Sheets

ROTATABLE BASE MULTI-AXIAL SCREW ASSEMBLY

FIELD OF INVENTION

Embodiments of the invention relate to implants used for correction of orthopedic injuries or deformities, and more specifically, but not exclusively, relate to multi-axial screws implanted in bone for stabilizing longitudinal support members.

BACKGROUND

Typical implant systems include several pieces, which may be associated or useful with only specific other pieces. Among such pieces are screws, hooks rods, plates and similar longitudinal members for supporting, holding and/or correcting one or more bones. Such longitudinal members can be fastened to bones via direct or indirect connection to hooks, screws, bolts or other fasteners, and may be linked to each other by a variety of connectors. In the spinal field, for example, screws or other fasteners can be attached to two or more vertebrae, the vertebrae can be adjusted into their normal or a therapeutically better position, and longitudinal members are connected to the fasteners so that the vertebrae are held in the normal or therapeutically improved position.

Accordingly, known bone screws, hooks, clamps and other bone fasteners or fixation devices can be connected or adjoined to a particular bone or bones as a connection between the remainder of the implant and the bone(s). Where a rod is used as a support and stabilizing member, commonly a series of two or more screws are inserted into two or more vertebrae to be instrumented. A rod is then placed within or coupled to the heads of the screws, or is placed within a connecting device that links the rod and a screw head, and the connections are tightened. In this way, a rigid supporting structure is fixed to the vertebrae, with the rod providing the support that maintains and/or promotes correction of the vertebral malformation or injury.

Some devices allow one or more degrees of freedom between a fastening portion or fastening member and a receiving portion or member, reducing the required precision of placement of the fixation device, since a head portion of the fixation device is multi-axially positionable around the bone-threaded or hook portion. The head can thus be positioned so as to easily receive the rod, limiting or removing much of the positioning difficulty inherent in prior devices. However, such multi-angle positioning between the fastening portion and the receiving portion for every relative orientation of those parts may create difficulty in fixing the screws in place during surgery.

The description herein of problems and disadvantages of known apparatuses, methods, and devices is not intended to limit the invention to the exclusion of these known entities. Indeed, embodiments of the invention may include, as a part of the embodiment, portions or all of one or more of the known apparatus, methods, and devices without suffering from the disadvantages and problems noted herein.

SUMMARY OF THE INVENTION

An aspect of the invention may include a multi axial screw assembly comprising a bone anchoring member, a receiver member, a base member and a crown. The receiver member has a channel configured to receive a rod and an aperture extending along a central axis of the receiver member. The aperture is configured to receive the base member. The aperture is generally cylindrical and has a diameter. The receiver member also has an internal groove. The base member is received within the aperture of the receiver member. The base member has a deflectable ring configured to mate with the internal groove of the receiver member and a slot configured to allow the deflectable ring to compress to a diameter less than the diameter of the aperture. The base member may be compressed and axially received within the receiver member and then released to engage the groove of the receiver member thereby axially restraining the base member relative to the receiver member while allowing for relative rotation between the base member and the receiver member. The crown is configured to be received within the receiver member along the central axis of the receiver member. The crown has an outer surface that is received within the base member to maintain the diameter of the deflectable ring greater than the diameter of the aperture.

Another aspect of the invention may include a method of assembling a multi-axial screw assembly having a rotating base. The method steps may orient a receiver member over a crown. Another step orients a crown over a bone anchoring member. The bone anchoring member is inserted through a base member. Another step axially receives a portion of the base member within an aperture in the receiver member while radially compressing a portion of the base member. An inner groove on the receiver member engages with the base member. A step provides axially receiving a portion of the crown within the base member to fix the axial motion of the base member with respect to the receiver member while allowing the base member to rotate relative to the receiver member.

Yet another aspect of the invention provides a method of implanting a multi-axial screw. A step provides fixing a bone anchoring member seated in a base member to bone. Another step orients a receiver member over the bone anchoring member. A portion of the base member is axially received within an aperture in the receiver member while a portion of the base member is radially compressed. A step provides engaging an inner groove on the receiver member with the base member. Another step axially receives a portion of the crown within the base member after the base member is engaged with the inner groove of the receiver member. The crown may fix the axial motion of the base member with respect to the receiver member while allowing the base member to rotate relative to the receiver member.

Additional aspects and features of the present disclosure will be apparent from the detailed description and claims as set forth below.

DETAILED DESCRIPTION

Figure 1:
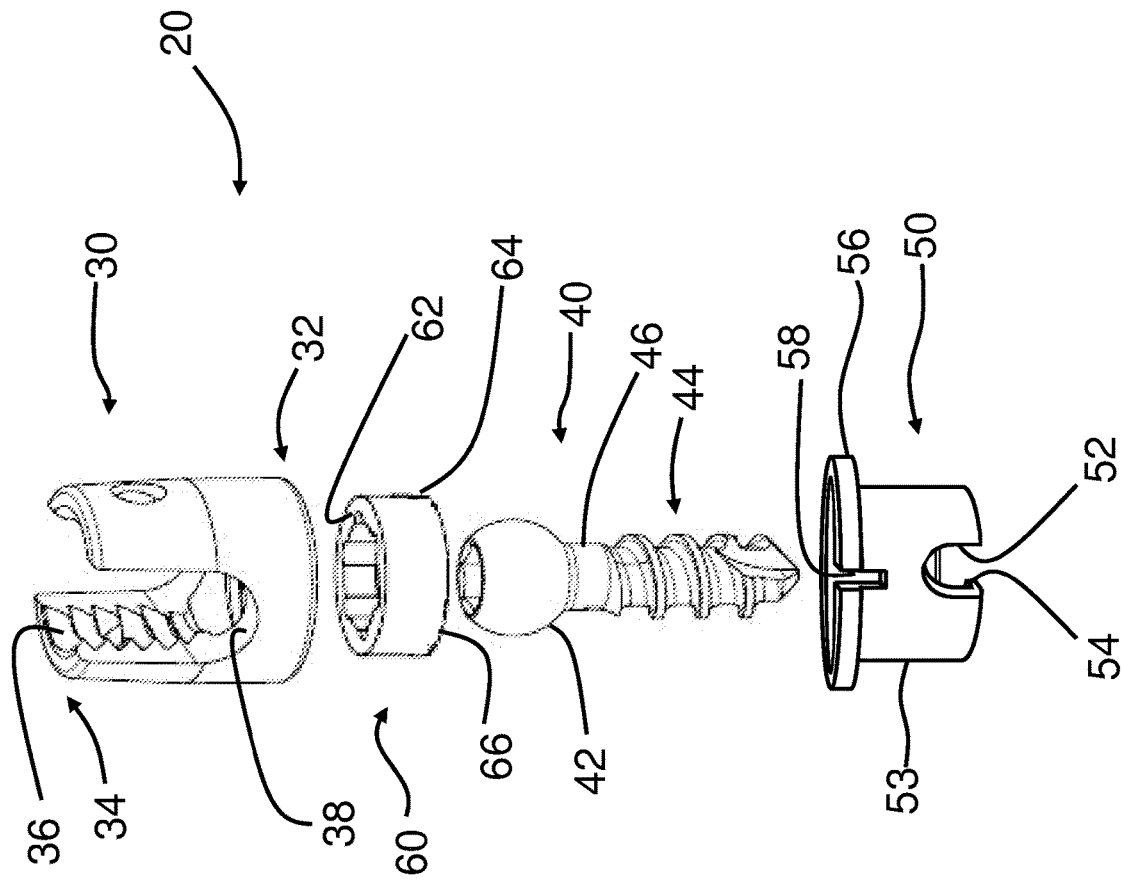
FIG. 1 is an exploded view of a multi-axial screw according to an aspect of the invention.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 is an exploded view of a multi-axial screw according to an aspect of the invention. Multi-axial screw assembly 20 includes a receiver member 30, a bone anchoring member 40, a base member 50 and a crown 60. The assembly 20 is configured such that the bone anchoring member 40 is captured between the base member 40 and the crown 60 along a central axis of the assembly 20. Receiver member 30 is also configured to accommodate a rod or other longitudinal member through a receiving channel 38 generally perpendicular to a central axis of the receiver member 30. In a specific embodiment, the receiver member 30 includes a lower portion 32 and a upper portion 34, a threaded portion 36 at or near upper portion 34 receives a compression member (for example, a set screw or other element with external threads) to capture the rod within the receiver member 30. In another embodiment, a threaded portion may be outside of a receiver member if an external compression member is used. Alternatively, receiver member could be externally and/or internally configured for compression members using snapping, twisting or other types of closures. An internal groove 39 (shown in FIG. 2) may receive the base member 50.

The bone anchoring member 40 includes a head portion 42, a threaded shaft 44, and a neck portion 46. The head portion 42 rests in the base member 50 of the assembly 20. The crown 60 may contact the head portion 42 of the bone anchoring member 40. As the force of the contact of the head portion 42 with the crown 60 increases (as the head portion 42 is pressed upon the base member 50 of the assembly 20) the bone anchoring member 40 is held in place relative to the receiver member 30.

The base member 50 has a cutout 52. The cutout 52 interrupts a side wall 53 and a seat 54 of the base member 50. A deflectable ring 56 located at the top of the base member 50 is received in the internal groove 39 of the receiver 30. The deflectable ring 56 axially fixes the base member 50 within the receiver 30 while allowing relative rotation between these parts 30 and 50. A slot 58 in the deflectable ring 56 and the side wall 53 allows the deflectable ring 56 to be compressed when installed in the receiver 30. Other embodiments may include a plurality of slots so that the deflectable ring 56 of the base member 50 may uniformly or symmetrically compressed within the receiver member 30. The seat 54 of the base member 50 provides a lower surface for the bone anchoring member 40 to rest.

Crown 60 includes an upper surface 62, a side wall 64, and an undersurface 66. The crown 60 is sized to fit within receiver member 30 so that crown 60 has some freedom of axial movement within the receiver member 30. The upper surface 62 may project above the receiving channel 38 of the receiver member 30. The crown 60, then, may be pressed by a rod in the receiving channel 38 toward the bone anchoring member 40. The axial movement of the crown 60 in the receiver 30 can then lock the bone anchoring member 40 between the crown 60 and the base member 50. The upper surface 62 may also have a tool receiving channel. The tool receiving channel may allow a tool to extend along the axis of the assembly 20 and engage the bone anchoring member 40. The bone anchoring member 40, then, may be advanced into bone through the receiver 30 and base member 50. The crown 60 may be received within the receiver member 30 along the central axis. The receiver member 30 may have surfaces that retain the crown 60 within the receiver 30.

The undersurface 66 is preferably configured to accommodate at least a part of head portion 42 of bone anchoring member 40. For example, undersurface 66 may be shaped (e.g. spherical, rounded, conical, or otherwise) to allow relative movement between crown 60 and part or all of head portion 42 of bone anchoring member 40. In the embodiment in which both undersurface 66 and head portion 42 have a rounded or spherical portion, undersurface 66 may have substantially the same or greater diameter as head portion 42.

The diameter of the crown 60 may be sized approximately equal to the inner diameter of the base member 50. The crown 60, then, when axially inserted within the base member 50, may keep the base member 50 from compressing and disengaging from the receiver member 30. The slot 58 may retain its shape when the crown 60 is seated in the base member 50. The side wall 64 of the crown 60 creates an interference in the base member 50. The interference holds the deflectable ring 56 within the groove 39 of the receiver member 30.

Figure 2:
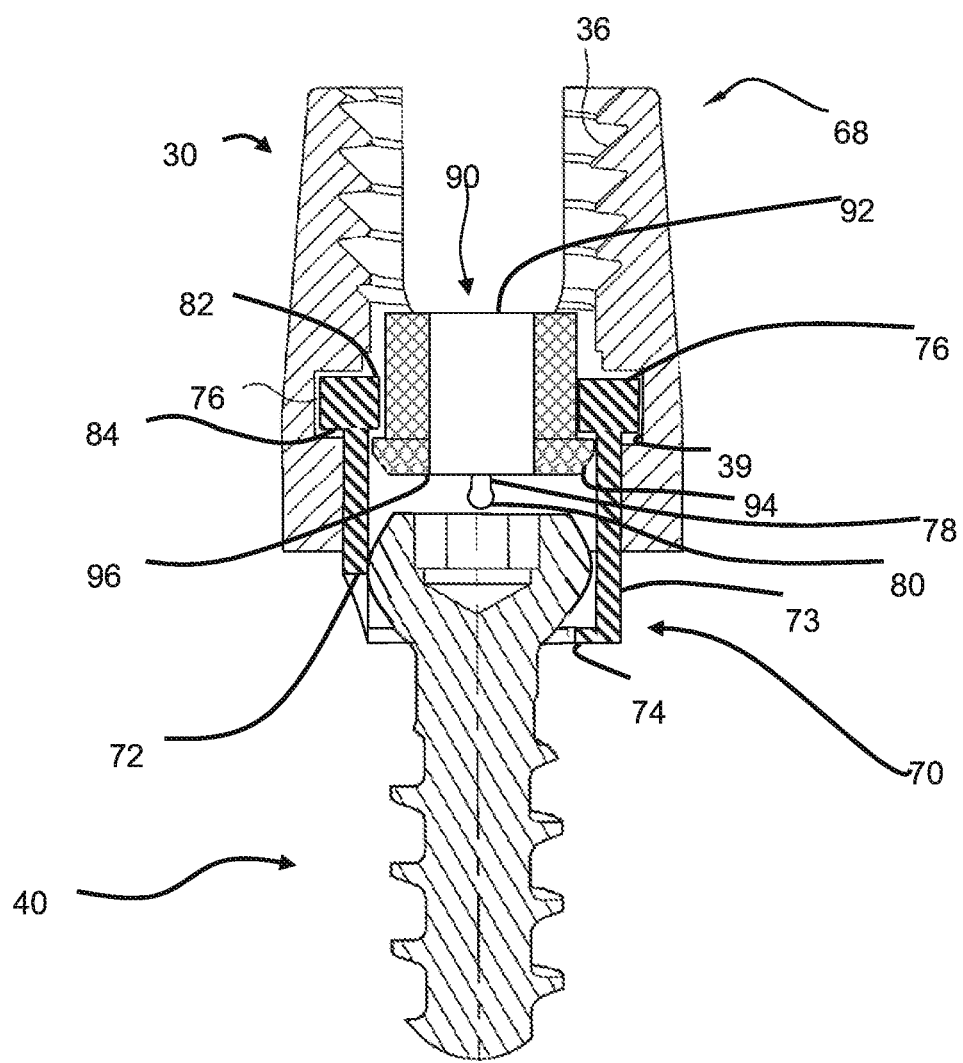
FIG. 2 is a cross-sectional view of another embodiment of a multi-axial screw according to an aspect of the invention.

Turning now to FIG. 2, FIG. 2 is a cross-sectional view of another embodiment of a multi-axial screw assembly 68 according to an aspect of the invention. A base member 70 and crown 90 vary from the base member 50 and crown 60 of FIG. 1. The crown 90 may have a channel 96 passing through an upper surface 92 and a plug ring 94. When the assembly 68 is assembled, the base member 70 is compressed into the receiver member 30. The crown 90 is then passed through the receiver member 30 and received in the base member 70 (as further described below). Alternatively, if the assembly 68 is assembled during a surgery, the bone anchoring member 40 may be implanted in bone with the base member 70, and then the crown 90 and receiver member 30 compressed into place after the bone anchoring member 40 is seated in the bone.

The base member 70 varies from the base member 50 of FIG. 1. The base member 70 includes a cutout 72, a side wall 73, a seat 74, a deflectable ring 76, a slot 78, slot relief 80, an inner overhang 82 and an outer over hang 84. The inner overhang 82 may capture the crown 90 within the assembly 68 after the crown 90 is dropped through the receiver 30. The outer overhang 84, similar to the function of the deflectable ring 56 in FIG. 1, captures the base member 70 in the receiver member 30.

The diameters of the crown 90, receiver member 30 and base member 70 are sized to fix the assembly 68 along its central axis while allowing rotational movement between the receiver member 30 and the base member 70. The outer diameter of the deflectable ring 76 is greater than the inner diameter of the receiver member 30, but less than the diameter of the internal groove 39 in the receiver member 30. This allows the base member 70 to be axially captured within the receiver member 30 but still rotate freely. The size of the slot 78 in the base member 70 is sized to allow the diameter of the base member 70 be compressed to a diameter less than the inner diameter of the receiver member 30 so that the base member 70 may be inserted into the receiver member 30. The diameter of the plug ring 94 is greater than the diameter of the inner overhang 82 of the deflectable ring 76, but less than the inner diameter of the receiver member 30. This allows for the crown 90 to be received in the base member 70 from the receiver member 30 but be captured by the inner overhang 82 from disconnecting from the assembly 68. The plug ring 94 may also outwardly (radially) deflect the deflectable ring 76 into the groove 39 as the crown 90 is axially received within the base member 70.

In contrast, in the embodiment of FIG. 1, the side wall 64 of crown 60 has a generally uniform diameter equal to the inner diameter of the base member 50. The crown 60 is received within the receiver member 30 and the base member 50. The crown 60 may be retained within the base member 50 by a rod received in the receiver member 30. The crown 90 of FIG. 2 is retained by the inner overhang 82 of the deflectable ring 76. The plug ring 94 may be a continuous ring around the outside of the crown 90 or may be tabs radially oriented around the crown.

The foregoing detailed description is provided to describe the invention in detail, and is not intended to limit the invention. Those skilled in the art will appreciate that various modifications may be made to the invention without departing significantly from the spirit and scope thereof. Furthermore, it is understood that all spatial references are for illustrative purposes only and can be varied within the scope of the disclosure.

The invention claimed is:

1. A multi axial screw assembly, comprising:
   a) a bone anchoring member extending between a head and a shaft;
   b) a receiver member having a channel configured to receive a rod and an aperture extending along a central axis of the receiver member, the aperture being generally cylindrical and having a diameter, the receiver member further having an internal groove with a top and bottom surface;
   c) a base member received within the aperture of the receiver member, the base member extending along an axis between a deflectable ring and a second end surface, the deflectable ring being configured to mate with the top and bottom surfaces of the internal groove of the receiver member and a slot within the deflectable ring configured to allow the deflectable ring to compress to a diameter less than the diameter of the aperture such that the base member may be compressed and axially received within the receiver member and then released to engage the groove of the receiver member thereby axially restraining the base member relative to the receiver member while allowing for relative rotation between the base member and the receiver member, the slot extending through the deflectable ring without extending through the second end surface, the base member including a cutout extending through the second end surface without extending through the deflectable ring, the base member including a sidewall extending between the deflectable ring and the second end surface and having a uniform outer diameter therebetween; and
   d) a crown configured to be received within the receiver member along the central axis of the receiver member, the crown having an outer surface that is received within the base member to maintain the diameter of the deflectable ring greater than the diameter of the aperture,
   wherein the bone anchoring member is movable between a first position in which the shaft extends parallel to the axis and a second position in which the shaft extends through the cutout at an angle that is transverse to the axis.

2. The multi axial screw assembly of claim 1, wherein the channel is configured along a first end of the receiver member, the crown is received in the first end of the receiver member.

3. The multi axial screw assembly of claim 2, wherein the deflectable ring has an inner overhang having a diameter less than an inner diameter of the side wall of the base member.

4. The multi axial screw assembly of claim 3, wherein the crown has a plug ring on a lower portion of the crown, the plug ring having a diameter larger than the diameter of the inner overhang of the deflectable ring.

5. The multi axial assembly of claim 4, wherein the crown has an upper portion with a diameter less than the inner diameter of the deflectable ring of the base member, the upper portion extending into the channel of the receiver member when the plug ring of the crown is within the base member.

6. The multi axial assembly of claim 4, wherein the plug ring is a continuous ring around the crown.

7. The multi axial screw assembly of claim 1, wherein the crown has an undersurface and the bone anchoring member has a head portion, the undersurface of the crown having a radius of curvature generally equal to or larger than a radius of curvature of the head portion of the bone anchoring member.

8. The multi axial screw assembly of claim 1, wherein:
   the top surface and the bottom surface extend perpendicular to the longitudinal axis, the top and bottom surfaces defining the internal groove;
   an upper surface of the deflectable ring engages the top surface; and
   a lower surface of the deflectable ring engages the bottom surface.

9. The multi axial screw assembly of claim 1, wherein the slot and the cutout are aligned.

10. The multi axial screw assembly of claim 1, wherein the slot extends parallel to the axis.

11. The multi axial screw assembly of claim 1, wherein the cutout is U-shaped.

12. The multi axial screw assembly of claim 1, wherein:
   the receiver member includes an opening extending through a distal end surface of the receiver member that is in communication with the aperture;
   a maximum diameter of the opening is greater than a maximum diameter of the head.

13. The multi axial screw assembly of claim 1, wherein the head is substantially spherical, an outer surface of the head being free of any projections.

14. The multi axial screw assembly of claim 1, wherein the slot extends through inner and outer surfaces of the deflectable ring.

15. The multi axial screw assembly of claim 1, wherein the diameter of the deflectable ring is less than a diameter of the internal groove in the receiver member.

16. A method of assembling a multi-axial screw assembly having a rotating base, comprising the steps of:
   orienting a receiver member over a base member;
   inserting a bone anchoring member through the base member;
   axially receiving a portion of the base member within an aperture in the receiver member while radially compressing a portion of the base member, the base member extending along an axis between a deflectable ring and a second end surface, the base member including a slot extending through the deflectable ring without extending through the second end surface and a cutout extending through the second end surface without extending through the deflectable ring, the base member including a sidewall extending between the deflectable ring and the second end surface and having a uniform outer diameter therebetween;
   engaging an inner groove on the receiver member with the base member such that a shaft of the bone anchoring member extends parallel to the axis, the deflectable ring configured for engagement with a to surface and a bottom surface of the inner groove disposed in the receiver;

axially receiving a portion of a crown within the base member to fix axial motion of the base member with respect to the receiver member while allowing the base member to rotate relative to the receiver member; and rotating the shaft relative to the receiver member such that the shaft extends through the cutout at an angle that is transverse to the axis.

17. The method of assembling a multi-axial screw assembly of claim 16, wherein the axially receiving step further comprises radially outwardly projecting the deflectable ring of the base member into the groove of the receiver member.

18. The method of assembling a multi-axial screw assembly of claim 16, further comprising engaging a head of the bone anchoring member with the crown to maintain the shaft at the angle that is transverse to the axis.

19. A method of implanting a multi-axial screw, comprising the steps of:

fixing a bone anchoring member seated in a base member to bone, the base member extending along an axis between a deflectable ring and a second end surface, the base member including a slot extending through the deflectable ring without extending through the second end surface and a cutout extending through the second end surface without extending through the deflectable ring, the base member includes a seat adjacent the second end surface and extending perpendicularly inward from the sidewall;

orienting a receiver member over the base member;

axially receiving a portion of the base member within an aperture in the receiver member while radially compressing a portion of the base member;

engaging an inner groove on the receiver member with the base member such that a shaft of the bone anchoring member extends parallel to the axis and is spaced apart from the cutout;

axially receiving a portion of a crown within the base member after the base member is engaged with the inner groove of the receiver member so that the crown fixes the axial motion of the base member with respect to the receiver member while allowing the base member to rotate relative to the receiver member; and rotating the shaft relative to the receiver member such that the shaft extends through the cutout at an angle that is transverse to the axis.

20. The method of assembling a multi-axial screw assembly of claim 19, wherein the axially receiving step further comprises radially outwardly projecting the deflectable ring of the base member into the groove of the receiver member.

* * * * *

UNITED STATES PATENT AND TRADEMARK OFFICE
CERTIFICATE OF CORRECTION

PATENT NO. : 9,603,630 B2
APPLICATION NO. : 13/097977
DATED : March 28, 2017
INVENTOR(S) : Farris Page 1 of 1

It is certified that error appears in the above-identified patent and that said Letters Patent is hereby corrected as shown below:

On the Title Page

In item (75), under "Inventor", in Column 1, Line 1, delete "Robert A" and insert -- Robert A. --, therefor.

In the Specification

In Column 3, Line 8, delete "base member 40" and insert -- base member 50 --, therefor.

In Column 5, Line 6, delete "be tabs" and insert -- be tabbed --, therefor.

In the Claims

In Column 6, Line 3, in Claim 5, delete "assembly" and insert -- screw assembly --, therefor.

In Column 6, Line 9, in Claim 6, delete "assembly" and insert -- screw assembly --, therefor.

In Column 7, Line 1, in Claim 16, delete "with a to" and insert -- with a top --, therefor.

In Column 7, Line 9, in Claim 16, delete "the shaft" and insert -- a shaft of the bone anchoring member --, therefor.

In Column 8, Lines 22-23, in Claim 20, delete "The method of assembling a multi-axial screw assembly of claim" and insert -- The method of implanting a multi-axial screw assembly of claim --, therefor.

Signed and Sealed this
Twenty-third Day of October, 2018

Andrei Iancu
*Director of the United States Patent and Trademark Office*